United States Patent [19]

Jansen

[11] Patent Number: 5,233,107
[45] Date of Patent: Aug. 3, 1993

[54] PROCESS FOR THE PURIFICATION OF CHLOROFLUOROHYDROCARBONS

[75] Inventor: Rolf-Michael Jansen, Kelkheim, Fed. Rep. of Germany

[73] Assignee: Hoechst Aktiengesellschaft, Frankfurt am Main, Fed. Rep. of Germany

[21] Appl. No.: 872,783

[22] Filed: Apr. 28, 1992

[30] Foreign Application Priority Data

Apr. 27, 1991 [DE] Fed. Rep. of Germany ....... 4113907

[51] Int. Cl.$^5$ .............................................. C07C 17/38
[52] U.S. Cl. .................................................. 570/179
[58] Field of Search ......................................... 570/179

[56] References Cited

U.S. PATENT DOCUMENTS

| | | |
|---|---|---|
| 3,696,156 | 10/1972 | Weeks . |
| 4,906,796 | 3/1990 | Yates . |
| 4,922,044 | 5/1990 | Yates et al. . |
| 4,940,824 | 7/1990 | Yates .................................. 570/179 |
| 4,940,825 | 7/1990 | Yates . |
| 4,950,816 | 8/1990 | Ting ................................... 510/179 |

FOREIGN PATENT DOCUMENTS 0370688 5/1990 European Pat. Off. .

*Primary Examiner*—Alan Siegel

[57] ABSTRACT

The invention relates to a process for removing olefinic impurities from hydrogen-containing chlorofluorohydrocarbons (HCFCs) in which the contaminated HCFCs are passed in the gas phase at 200° to 400° C. over a zeolite.

14 Claims, No Drawings

PROCESS FOR THE PURIFICATION OF CHLOROFLUOROHYDROCARBONS

The present invention relates to a process for removing olefinic impurities from hydrogen-containing chlorofluorohydrocarbons. Hydrogen-containing chlorofluorohydrocarbons (HCFCs) are used as substitutes for the ozone-endangering fully-halogenated, i.e. hydrogen-free, chlorofluorocarbons (CFCs). However, in order to be able to use HCFCs in areas such as foamed plastics and refrigeration or as aerosols, undesired byproducts, which may be formed during synthesis, in some cases in trace elements, must be removed quantitatively. These byproducts are principally olefins, some of which are toxic.

A known method of removing some unsaturated impurities is adsorption on activated charcoal or zeolites. Thus, for example, U.S. Pat. No. 4,940,825 discloses a process for removing dichloroacetylene from R 141b (1,1-dichloro-1-fluoroethane) or vinyl chloride by adsorption at from $-20°$–$20°$ C. to $+60°$ C. on activated charcoal having a pore size of from 4.2 to 4.8 Ångström. U.S. Pat. No. 4,992,044 states that dichloroethylene and bromochloromethane are removed from chloroform at from $10°$ to $150°$ C. by adsorption on calcium chabazite. According to U.S. Pat. No. 4,906,796, R 1122 (difluorochloroethylene) is removed from R 134a (1,1,1,2-tetrafluoroethane) by adsorption at from $-10°$ to $100°$ C. on a zeolite or activated charcoal having a pore radius of from 3.8 to 4.8 Ångström. In general, however, olefins having more than two carbon atoms cannot be removed from HCFCs from the ethane series in this way. A further disadvantage is that the byproducts which build up to high levels in the adsorbent and may highly toxic must subsequently be disposed of at great expense. U.S. Pat. No. 3,696,156 describes another method in which olefinic impurities are removed from CFCs by passing the contaminated CFCs at from $180°$ to $250°$ C. over aluminum oxide which has been treated with alkali metal hydroxides or alkaline earth metal hydroxides. EP-A-370 688 discloses a similar method in which the olefin-contaminated CFCs are passed at temperatures of up to $300°$ C., preferably below about $250°$ C., over an amorphous metal oxide. Both these processes have the disadvantage that preparation in a constant quality of the solids used is only possible at great expense. In addition, some impurities are only degraded to a small extent.

The invention relates to a process for removing olefinic impurities of the formula $C_mH_nF_pCl_q$ where $m=2-3$, $n=1-4$, $p=1-6$, $q=0-4$ and $n+p+q=2m$, from hydrogen-containing chlorofluorohydrocarbons (HCFCs) of the formula $C_aH_bF_cCl_d$ where $a=2-3$, $b=1-5$, $c=1-7$, $d=0-4$ and $b+c+d=2a+2$, which comprises passing the contaminated chlorofluorohydrocarbons in the gas phase at temperatures of $200°$ to $400°$ C. and pressures of from 1 to 50 bar over a zeolite which, in the anhydrous and template-free form, has the formula $Z \cdot Al_2O_3 \cdot x(SiO_2)$ in which $Z=H$, $NH_4$, $M(I)_2O$, $M(II)O$ or $M(III)_2O_3$ where M(I) is an alkali metal, M(II) is an alkaline earth metal and M(III) is a rare earth metal having an atomic number from 57-71 in the Periodic Table of the Elements, and x is a number from 2 to 2000.

Particularly suitable HCFCs are:
1,1,1-trifluoro-2-chloroethane (R 133a), 1,1,1-trifluoro-2,2-dichloroethane (R 123), 1,1,1-2-tetrafluoroethane (R 134a), 1,1,1,2,2-pentafluoroethane (R 125) and 1,1,1,2,3,3,3-heptafluoropropane (R 227).

Examples of usual olefinic impurities are:
1,1-difluorochloroethene, 1,1-difluorodichloroethene, 1,2-difluoroethene, 1,1,2-trifluorochloroethene, 1H-pentafluoropropane, 2H-pentafluoropropene, 1,1,1,4,4,4-hexafluoro-2-chloro-2-butene and 2-trifluoromethyl-3,3,3-trifluoro-1-propene.

The contaminated HCFCs are preferably passed over the zeolite at from $250°$ to $350°$ C., in particular at from $290°$–$310°$ C. The pressure is preferably from 1-25 bar.

The zeolite is contained, for example, in a heatable glass tube, where the ratio between the tube diameter and the fill level of the zeolite is preferably from 1:5 to 1:15.

The gaseous, contaminated HCFC can be heated to the chosen reaction temperature over a short preheating zone. Relatively high-boiling HCFCs, such as R 123, must be converted into the gas phase in advance in a separate evaporator.

The gas flow rate during the reaction is preferably from 2-50 l/h. It is furthermore preferred to pass the contaminated HCFCs over the zeolite in a stream of inert carrier gas, such as $N_2$.

The zeolite employed has, in the anhydrous and templatefree form, the formula $Z \cdot Al_2O_3 \cdot x(SiO_2)$ where $Z=H$, $NH_4$, $M(I)_2O$, $M(II)O$ or $M(III)_2O_3$ in which M(I) is an alkali metal, M(II) is an alkaline earth metal and M(III) is a rare earth metal having an atomic number of 57-71. M(I) is preferably Li, Na or K, M(II) is preferably Ca, Ba or Sr, and M(III) is preferably La or Ce. Furthermore, x is a number from 2 to 2000, preferably from 2 to 200, in particular from 2 to 50. Said zeolites are described in Donald W. Breck, Zeolite Molecular Sieves, 1974, Wiley and Sons.

Particular preference is given to the use of H-ZSM 5 (U.S. Pat. No. 3,702,886), zeolite A (U.S. Pat. No. 2,882,243), zeolite X (U.S. Pat. No. 2,882,244) and zeolite Y (U.S. Pat. No. 3,130 007). Particularly suitable forms of zeolite A are 5 Ångström molecular sieve and in particular 10 Ångström molecular sieve.

The zeolite can be used either as a powder or in the form of moldings, for example beads or cylinders. If powders are used, the flow resistance is preferably reduced by mixing with glass or metal elements, for example Raschig rings or metal coils, in order to achieve suitable flow rates.

The zeolite can, if necessary, be regenerated using air or oxygen at elevated temperatures.

It is preferred to add continuously from 0.5 to 10% by volume of oxygen or air to the contaminated HCFCs before they are passed over the zeolite; this keeps coking at a very low level.

The olefinic impurities are clearly degraded completely or very substantially during the process according to the invention, in contrast to the adsorption processes mentioned above, in which the impurities must subsequently be removed from the adsorbent and disposed of.

The examples below are intended to illustrate the invention in greater detail.

EXAMPLES 1-4:

50 ml of 1,1-Dichloro-2,2,2-trifluoroethane (R 123) containing 1,500 ppm of 1,1,1,4,4,4-hexafluoro-2-chloro-2-butene (R 1326) were passed at $300°$ C. in a stream of nitrogen whose flow rate (25.2 l/h) was controlled by means of a mass flow regulator, through a glass tube (internal diameter = 20 mm, length = 100 cm) packed with about 50 g of zeolite (fill level about 30 cm) and subsequently condensed. The R 1326 content in the R 123 was determined by gas chromatography. The results are shown in Table 1.

TABLE 1

| Example | Zeolite | Condensate [ml] | Reaction duration [h] | R 1326 content [ppm] | Performance [ml/h] |
|---------|---------|-----------------|------------------------|-----------------------|---------------------|
| 1 | HZSM 5 | 46 | 4 | 45 | 12.5 |
| 2 | zeolite Y | 42 | 2 | below the detection limit | 25 |
| 3 | 5Å molecular sieve | 40 | 3 | 258 | 16.6 |
| 4 | 10Å molecular sieve | 41 | 3 | below the detection limit | 16.6 |

Comparative Examples 1–3

For comparison, the experiments of Examples 1–4 were carried out with the zeolite replaced by $SiO_2$, $\gamma$-$Al_2O_3$ or activated charcoal (BET specified surface area: 1250 m²/g). The results are shown in Table 2.

TABLE 2

| Comparative Example | Reactor packing | Condensate [ml] | Reaction duration [h] | R 1326 content [ppm] | Performance [ml/h] |
|---------------------|-----------------|------------------|-------------------------|------------------------|----------------------|
| 1 | Activated charcoal | 44 | 3 | 1343 | 16.6 |
| 2 | $SiO_2$ | 41 | 4 | 2640 | 12.5 |
| 3 | $\gamma$-$Al_2O_3$ | 41 | 4 | 1290 | 12.5 |

I claim:

1. A process for removing olefinic impurities of the formula $C_mH_nF_pCl_q$ where $m=2-3$, $n=1-4$, $p=1-6$, $q=0-4$ and $n+p+q=2m$, from hydrogen-containing chlorofluorohydrocarbons of the formula $C_aH_bF_cCl_d$ where $a=2-3$, $b=1-5$, $c=1-7$, $d=0-4$ and $b+c+d=2a+2$, which comprises passing the contaminated chlorofluorohydrocarbons in the gas phase at temperatures of 200° to 400° C. and pressures of from 1 to 50 bar over a zeolite which, in the anhydrous and template-free form, has the formula $Z \cdot Al_2O_3 \cdot x\,(SiO_2)$ in which $Z = H$, $NH_4$, $M(I)_2O$, $M(II)O$ or $M(III)_2O_3$ where $M(I)$ is an alkali metal, $M(II)$ is an alkaline earth metal and $M(III)$ is a rare earth metal having an atomic number from 57–71 in the Periodic Table of the Elements, and x is a number from 2 to 2000.

2. The process as claimed in claim 1, which is carried out at from 250° to 350° C.

3. The process as claimed in claim 1, which is carried out at from 290° to 310° C.

4. The process as claimed in claim 1, wherein the contaminated chlorofluorohydrocarbons are passed over the zeolite in a stream of carrier gas.

5. The process as claimed in claim 1, wherein from 0.5 to 10% by volume of oxygen or air is continuously metered into the contaminated chlorofluorohydrocarbons before they are passed over the zeolite.

6. The process as claimed in claim 1, wherein the zeolite employed is H-ZSM 5, zeolite A, zeolite X or zeolite Y.

7. The process as claimed in claim 1, wherein olefinic impurities are removed from one of the hydrogencontaining chlorofluorohydrocarbons 1,1,1-trifluoro-2-chloroethane (R 133a), 1,1,1-trifluoro-2,2-dichloroethane (R 123), 1,1,1,2-tetrafluoroethane (R 134a), 1,1,1,2,2-pentafluoroethane (R 125) or 1,1,1,2,3,3,3-heptafluoropropene (R 227).

8. The process as claimed in claim 1, wherein the pressure is from 1 to 24 bar.

9. The process as claimed in claim 1, wherein the zeolite is contained in a heatable glass tube, where the ratio between the tube diameter and the fill level of the zeolite is from 1:5 to 1:15.

10. The process as claimed in claim 1, wherein a gas flow rate during the reaction is from 2–50 l/h.

11. The process as claimed in claim 4, wherein the carrier gas is nitrogen.

12. The process as claimed in claim 1, wherein x is 2 to 200.

13. The process as claimed in claim 12, wherein x is 2 to 50.

14. The process as claimed in claim 1, wherein M (I) is Li, Na or K; M (II) is Ca, Ba or Sr; and M (III) is La or Ce.

* * * * *